United States Patent [19]

Lovelock

[11] 4,388,411
[45] Jun. 14, 1983

[54] APPARATUS AND METHOD FOR DETECTING FLUID

[75] Inventor: James E. Lovelock, Launceston, England

[73] Assignee: Hewlett-Packard Company, Palo Alto, Calif.

[21] Appl. No.: 258,843

[22] Filed: Apr. 29, 1981

[51] Int. Cl.³ .................... G01N 27/14; G01N 21/72; G01N 33/00

[52] U.S. Cl. .................................. 436/149; 422/54; 422/90; 422/93; 422/94; 422/98; 436/52; 436/153; 436/154; 436/177; 436/178; 250/304; 250/379; 250/383; 250/389; 73/19

[58] Field of Search ............... 23/232 E; 422/90, 93, 422/98, 68, 52, 54; 250/304, 379, 380, 382, 383, 389; 73/61.1 R, 19; 55/16, 71, 158; 436/52, 149, 154, 153, 177, 178

[56] References Cited

U.S. PATENT DOCUMENTS 3,367,850  2/1968  Johnson ............... 73/61.1 R
3,638,396  2/1972  Lovelock ............... 55/16
3,725,009  4/1973  Lovelock ............. 23/23 LE
3,791,106  2/1974  Haley .................. 55/158
3,909,218  9/1975  Kamura et al. ......... 55/158
3,967,933  7/1976  Etess et al. ........... 23/232 E
3,997,297  12/1976 Jenkins et al. ......... 422/93
4,019,863  4/1977  Jenkins et al. ......... 422/93
4,304,752  12/1981 Jenkins et al. ......... 422/98

Primary Examiner—Michael S. Marcus
Attorney, Agent, or Firm—Donald N. Timbie

[57] ABSTRACT

The invention relates to apparatus for detecting a constituent gas in a gas flow. Means is provided for removing the constituent gas from a sample flow and directing this sample flow together with a reference flow containing the constituent gas through an equilibrator means wherein contaminants can be removed before the sample gas and the reference gas are compared in detector means, for example, an electron capture detector. The apparatus and method are also applicable to the detection of a liquid in a flow thereof.

28 Claims, 15 Drawing Figures

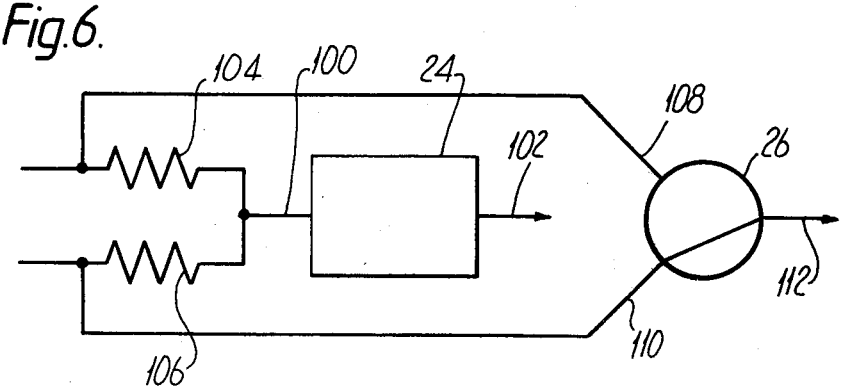
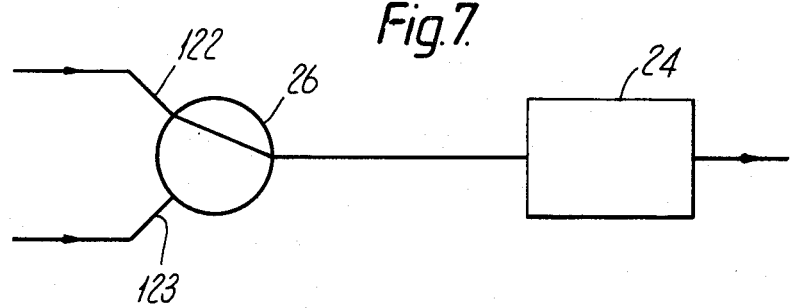
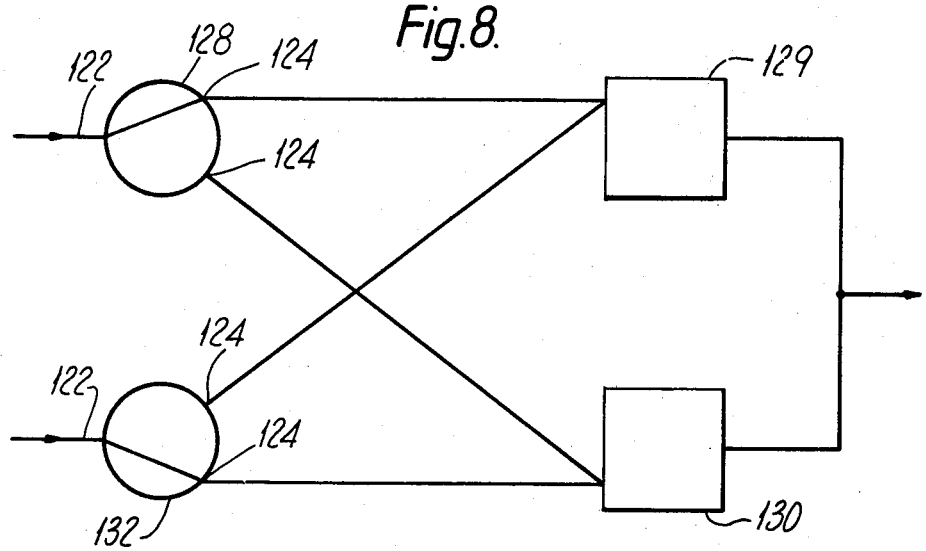

APPARATUS AND METHOD FOR DETECTING FLUID

The present invention is concerned with improvements in or relating to method and apparatus for regulating gas flow in the detection of a constituent in the gas, and is more specifically concerned with the detection, per se, of the constituent.

The invention is particularly applicable to the detection of constituent gas which is present in the carrier gas in amounts which are as low as one part in $10^{12}$, and where the carrier gas is maintained at a constant flow rate through a detector of as low as 0.1 cc per minute.

As will be readily recognized by those skilled in the art, detection of very small quantities of a constituent gas in a gas flow is very difficult due to the sensitivity of the detecting instruments currently available to the presence of gases in a gas flow which it is not desired to detect. A detecting system of a type with which the present invention is concerned is disclosed in U.K. Patent Application No. 1,482,611.

However, practice and experiment has shown that in the monitoring of signals, by which the presence of a gas constituent in a gas flow can be detected, using an arrangement such as is disclosed in U.K. Pat. No. 1,482,611, especially where the extreme end of the sensitivity range is used, i.e. $1 \times 10^{-12}$, detection of a constituent gas can be rendered very difficult, at the very least, due to the presence of contaminants which can be present in a gas flow in vapour or gaseous form issuing from, for example, a gas chromatograph column. These contaminants may completely mask the presence of a constituent gas which it is desired to detect thereby leading to erroneous results.

The present invention provides apparatus for use in detecting a constituent fluid in a sample flow of fluid, also containing at least one contaminant, the apparatus comprising first and second conduit means each having an inlet and an outlet and being formed of a material which is permeable to the at least one contaminant, enclosure means for enclosing the first and second conduit means substantially along the length thereof, the enclosure means having an inlet and an outlet whereby a diluent fluid can be passed through the enclosure means to remove any at least one contaminant diffused from the first and second conduit means into the enclosure means; detector means having an inlet and an outlet; and valve control means for alternately allowing the sample flow of fluid from the first conduit means to pass through the detector means, when the valve control means is in a first condition, and a reference flow of fluid from the second conduit means to pass through the detector means, when the valve control means is in a second condition.

In a first embodiment of an apparatus as set forth in the last preceding paragraph the detector means has a second inlet, and the valve control means has a first inlet, a second inlet and an outlet, the first conduit means being connected to the first inlet of the detector means and to the first inlet of the valve control means, and the second conduit means being connected to the second inlet of the detector means and to the second inlet of the valve control means, whereby, when the valve control means is in its first condition, the reference flow of fluid passes through the valve control means to its outlet, and, when the valve control means is in its second condition, the sample flow of fluid passes through the valve control means to its outlet.

In a second embodiment of an apparatus as set forth in the last preceding paragraph but one the outlet of the detector means provides a second inlet, and the valve control means has a first inlet, a second inlet and an outlet, the first conduit means being connected to the first inlet of the detector means and to the first inlet of the valve control means and the second conduit means being connected to the second inlet of the detector means and to the second inlet of the valve means, whereby, when the valve control means is in its first condition the sample flow of fluid passes from the first inlet to the second inlet of the detector means and, in admixture with reference flow of fluid, passes through the valve control means to its outlet, and, when the valve control means is in its second condition, the reference flow of fluid passes from the second inlet to the first inlet of the detector means and, in admixture with the sample flow of fluid, passes through the valve control means to its outlet.

In a third embodiment of an apparatus as set forth in the last preceding paragraph but two the valve control means has a first inlet, a second inlet and an outlet, the apparatus further comprising a first fluid restrictor having an outlet connected to the inlet of the detector means, and an inlet, and a second fluid flow restrictor having an outlet connected to the inlet of the detector means, and an inlet, the first conduit means being connected to the inlet of the first fluid flow restrictor and to the first inlet of the valve control means, and the second conduit means being connected to the inlet of the second fluid flow restrictor and to the second inlet of the valve control means.

A fourth embodiment of an apparatus as set forth in the last preceding paragraph but three may further comprise second detector means having an inlet and an outlet, the valve control means having an inlet, a first outlet and a second outlet, the first outlet being connected to the inlet of the first detector means and the second outlet being connected to the inlet of the second detector means. The fourth embodiment preferably further comprises second valve control means having an inlet and a first outlet and a second outlet, the first outlet of the second valve control means being connected to the first-mentioned detector means, and the second outlet of the second valve control means being connected to the second detector means, the two detector means each having an output and these outputs being connected in common, the inlet of the first valve control means being connected to the outlet of the first conduit means, and the inlet of the second valve control means being connected to the outlet of the second conduit means.

The or each valve means may comprise an electromagnetically controlled, movable-reed valve.

In a fifth embodiment of an apparatus as set forth in the last preceding paragraph but four the valve control means has a first inlet connected to the outlet of the first conduit means, a second inlet connected to the outlet of the second conduit means and an outlet connected to the inlet of the detector means.

In a sixth embodiment of an apparatus as set forth in the last preceding paragraph but five the valve control means has a first inlet, a second inlet and an outlet, the first conduit means being connected to the first inlet of the valve control means and to the inlet of the detector means, and the second conduit means being connected to the second inlet of the valve control means and to the inlet of the gas detector means.

An apparatus as set forth in any one of the last eight paragraphs may further comprise fluid reactor means capable of effecting a chemical change in the constituent fluid in the sample flow of fluid, and having an inlet and an outlet, connected to the first conduit means, whereby the sample flow of fluid is introduced into the fluid reactor means upstream of the first conduit means, dummy fluid reactor means being similarly connected to the inlet of the second conduit means.

In an apparatus as set forth in the last preceding paragraph fluid flow restrictor means may be connected to the inlet of each of the fluid reactor means and the dummy fluid reactor means.

In an apparatus as set forth in the last preceding paragraph but nine the detector means may be gas detector means for detecting the presence of a constituent gas in a sample flow of gas also containing at least one gaseous contaminant.

The material of the first and second conduit means is chosen according to the expected composition of the sample flow gas. Thus for example if the sample gas flow contains water and/or light polar molecules as contaminants, the material of the conduits might be "Nafion" (Trade Mark) which is manufactured by E. I. du Pont de Nemours & Co. Inc. If the contaminant is oxygen or the vapour of an organic substance, then a silicone rubber, such as dimethyl silicone, is suitable. Hydrogen can be removed by making the conduit means of palladium.

The present invention further provides a method of detecting a constituent fluid in a sample flow of fluid also containing at least one contaminant, the method comprising the steps of (a) directing the sample flow of fluid along first conduit means; (b) directing a reference flow of fluid along second conduit means; the first and second conduit means each being formed of a material which is permeable to the at least one contaminant and being enclosed substantially along the length thereof by enclosure means having an inlet and an outlet; (c) passing fluid through the enclosure means to wash out therefrom contaminant which has diffused through the first and second conduit means; (d) alternately directing the sample flow of fluid and the reference flow of fluid to fluid detector means; and (e) monitoring electrical signals from the fluid detector means to determine when the constituent fluid is present in the fluid detector means and when it is absent.

In the illustrative embodiments, step (d) is carried out by operating valve control means synchronized with the fluid detector means.

In carrying out a first illustrative method according to the present invention the detector means has a first inlet, a second inlet, and an outlet and the valve control means has a first inlet, a second inlet and an outlet, the first inlets of the detector means and the valve control means communicating with the second conduit means, whereby step (d) is carried out by directing the sample flow of fluid through the first conduit means and the first inlet and the outlet of the detector means while the reference flow of fluid is directed through the second conduit means and the second inlet and the outlet of the valve control means, and then by directing the sample flow of fluid through the first conduit means and the first inlet and the outlet of the valve control means, while the reference flow of fluid is directed through the second conduit means and the second inlet and the outlet of the detector means.

In carrying out a second illustrative method according to the present invention the detector means has a first connector, and a second connector, and the valve control means has a first inlet, a second inlet and outlet, the first connector, and the first inlet of the valve control means communicating with the first conduit means, and the second connector, and the second inlet of the valve control means communicating with the second conduit means, whereby the sample flow of fluid is directed through the first conduit means and the first and second connectors into the second conduit means while the reference flow of fluid is directed through the second conduit means and the second inlet and the outlet of the valve control means, and the sample flow of fluid is directed through the first conduit means and the first inlet and the outlet of the valve control means, while the reference flow of fluid is directed through the second conduit means and the first and second connectors into the first conduit means.

In carrying out a third illustrative method according to the present invention two valve control means and a second detector means are provided, each valve control means having an inlet and first and second outlets, and each detector means having an inlet and an outlet, the first outlet of both valve control means being connected to the inlet of the first detector means, and the second outlet of both valve control means being connected to the inlet of the second detector means, whereby step (d) is carried out by directing the sample flow of fluid through the first outlet of the first valve control means and through the first detector means while the reference flow through the second outlet of the second valve control means and through the second detector means, and by directing the sample flow of fluid through the second outlet of the first valve control means and through the second detector means, while the reference flow is directed through the first outlet of the second valve control means and through the first detector means.

Prior to carrying out step (a), the sample flow of fluid may be passed through fluid reactor means capable of effecting a chemical change in the constituent fluid in the sample flow; prior to carrying out step (b), the reference flow of fluid is then passed through dummy fluid reactor means.

The fluid may be gaseous.

Preferably the rate of flow of washing fluid through the enclosure means, in carrying out step (c), is such as to allow the quantities of any contaminant present in the first and second conduit means to become substantially equal.

There now follows a detailed description which is to be read with reference to the accompanying drawings of various apparatuses and methods according to the present invention; it is to be clearly understood that these illustrative apparatuses and methods have been selected for description to illustrate the invention by way of example and not by way of limitation.

In the accompanying drawings:

FIGS. 4 to 8 are schematic diagrams illustrating arrangements of valve control means and gas detector means for use in apparatus according to the invention;

Figure 1:
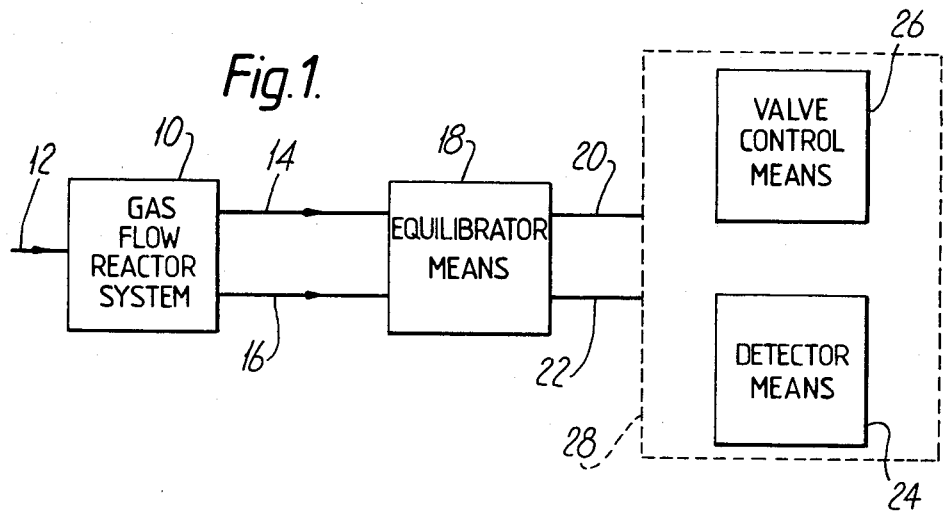
FIG. 1 is a block diagrammatic illustration of an apparatus according to the invention.

Referring firstly to FIG. 1, there is shown an apparatus according to the present invention for detecting the presence or absence of a constituent gas in a sample flow of gas also comprising one or more contaminant gases. The apparatus comprises a gas flow reactor system 10 having an inlet 12 and two outlets 14, 16 leading to an "equilibrator" 18. The equilibrator 18 has two outlets 20, 22 leading to detector means 24 and valve control means 26 which are shown enclosed in the broken line rectangle 28 for the reason discussed below.

Figure 2:
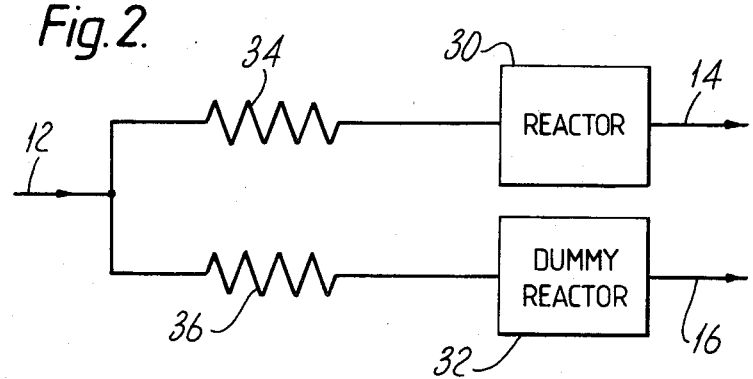
FIG. 2 is a schematic diagram of a gas flow reactor system of apparatus according to the invention.

The function of the gas flow reactor system 10, shown in more detail in FIG. 2, is to react upon the constituent gas in the sample flow by use of a reagent or a catalyst whereby to remove the constituent gas as such from the flow by breaking down the constituent gas into components which do not elicit a response when they pass through the detector means 24.

The reactor system of FIG. 2 comprises a first reactor means 30 and a dummy reactor means 32 each connected in series with a respective gas flow restrictor means 34, 36, connected to a common inlet 12. The gas flow restrictor means 34, 36 provide means whereby a uniform gas pressure can be developed at the inlet to each reactor means and thus a uniform rate of flow through the reactor means. The arrangement of the reactor system is such that flow of gas from the common inlet 12, from, say a gas chromatograph column, is divided substantially equally with half of the flow directed towards the first reactor means 30 and the other half being directed towards the dummy reactor means 32.

Figure 2A:
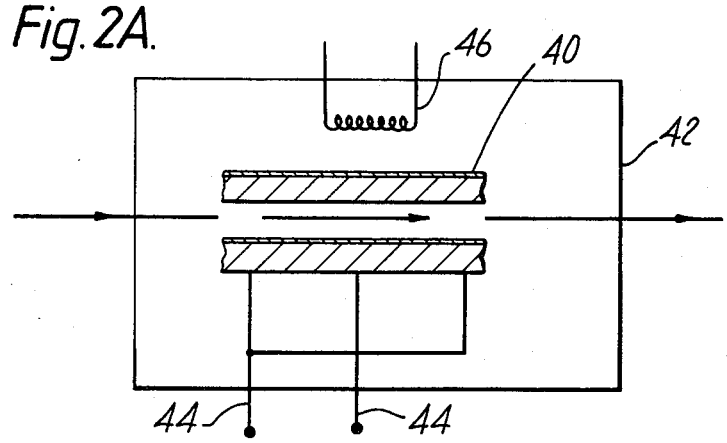
FIG. 2A is a schematic diagram of a reactor means of an apparatus according to the invention.

The reactor means 30 can take a number of different forms, as stated in the specification of U.K. Pat. No. 1,482,611 and re-stated here for convenience. One form is shown in FIG. 2A and comprises a thin wall metallic tube 40 with the gas flowing in the direction indicated by the arrows through the tube to the detector means. The tube is heated to direct resistance heating. By passing an electric current through the wall of the tube, by means of leads 44, the temperature can be increased rapidly from ambient temperature to about 250° C. or higher and maintained at that level for as long as is necessary. For cooling of the tube 40 when desired, the tube can be enclosed within a heat sink 42 the temperature of which can be controlled by a coil 46.

Alternatively, the tube can be formed from a material, such as glass, which is either non-conducting or a poor conductor of electricity. Heating can be by means of a filament, for example a platinum wire, extending inside the length of the tube. The temperature can be controlled by monitoring the electrical resistance of the filament.

Another form of reactor means 30 utilises a ferromagnetic wire coil maintained inside a glass or ceramic tube along which the sample flows to the detector. The tube itself is suspended in the coil of a radio-frequency oscillator. The wire coil can absorb energy rapidly from the radio-frequency field until the temperature of the coil reaches the Curie point. At this point the magnetic permeability of the coil falls suddenly and the absorbed energy falls rapidly so that the temperature of the coil is controlled at the Curie point. On switching off the oscillator the temperature falls rapidly. Conveniently use is made of a ferro-,agnetic wire coil with a Curie point in the temperature range 250° C. to 400° C.

Another form of reactor means 30 involves irradiating a heated quartz tube with ultra-violet radiation.

The nitroxy group: (O-NO$_2$) in nitro explosive gives an absorption band at about 270 nm in the ultra violet region. The rate of decomposition of nitro compounds is slow at about 125° C. but according to published papers the rate thereafter doubles with every 50° C. temperature rise. Thus the sample to the detector means is passed through a quartz tube maintained at an elevated temperature. Upon irradiation of the tube with ultra violet the nitro vapours are broken down into components which do not give rise to an output in the detector means. The ultra violet radiation is pulsed periodically by means of the oscillator. A similar effect can be achieved using a pulsed laser of high intensity.

Yet another form of reactor means 30 can utilise the strong electron capture properties of certain compounds. Upon capturing an electron, an electro-negative species forms a negative ion which either dissociates or discharges on positive ions or at an electrode resulting in the destruction of the electro-negative species and the production of non-electron capturing products.

Thus, the reactor means 30 can comprise an ionization chamber in which thermal electrons are produced in pulses. Such an ionization chamber can include a radiative source of $\alpha$, $\beta$ or other ionizing radiation and a pair of spaced apart electrodes. Conveniently the chamber can be cylindrical with the radioactive source formed into the wall of the cylinder with the gas flow over the length of the chamber. One electrode can be formed by the body of the chamber and the other electrode can be a wire extending along the axis of the chamber. The potential across the electrodes is switched periodically between high and low values, for example between 100 volts and zero.

When a sample gas flowing through such reactor means 30 to the detector means contains a strong electron absorber in addition to a weak electron absorber or absorbers, the probability of capture of electrons by the strong absorber approaches 100% whereas the probability of capture by the weak absorber or absorbers is very low. When a high potential is applied across the electrodes the electrons produced by the ionizing radiation are immediately attracted to the anode of the ionization chamber with little or no probability of capture. With a low or zero potential across the electrodes the electrons produced by the ionizing radiation are at thermal energies and are captured by the strong absorber with a probability approaching 100%. The weak absorber content of the gas flow into the detector means remains substantially constant. However, the strong absorber content fluctuates according to the changes in the potential across the electrodes of the reactor means 30. Hence a periodic switching of the potential across the electrodes of the reactor means 30 under control of the oscillator causes a periodic variation in the output of the following detector to distinguish the presence of the strong electron absorber in the gas flow.

As an alternative to the above, the reactor means 30 can comprise an ionization chamber in which thermal electrons are produced in pulses by irradiation of a photo-sensitive layer. Thus thermal electrons can be produced by irradiating a thin layer of material capable of emitting electrons by photo-emission with ultra violet light. A suitable material can be gold, silver or palladium, or an alloy of such materials. Such a photo-sensitive layer can be deposited by evaporation on the interior of the ionization chamber. Ultra-violet light can be periodically directed against the deposited photo-sensitive layer to produce a high electron density within the chamber, the pulsing of the light source being under the control of the oscillator. The electrons produced can have a half life of approximately 1 ms and can be removed by collision with the walls of the chamber or are swept out of the chamber with the gas flow. It is possible to control the electron density within the chamber such that it varies between a low value, for example zero, and a value sufficient to ensure substantially 100% probability of capture by strong absorbers in the gas flow. The reactor means 30 functions in the manner as described with reference to the preceding embodiment except that the electrons are periodically generated by flashing the ultra-violet light source.

The dummy reactor means 32 is substantially the same as the reactor means 30 only insofar as the path defined thereby through which gas must flow. However, the dummy reactor means 32 is not set up to react upon the gas to destroy or disrupt the constituent gas.

Thus two flows of gas emanate from the reactor system, one, the sample flow of gas, from the reactor means 30, and the other, a reference flow of gas, from the dummy reactor means 32. The reference flow of gas contains every constituent that was present in the gas when it was introduced at the inlet 12.

Figure 3:
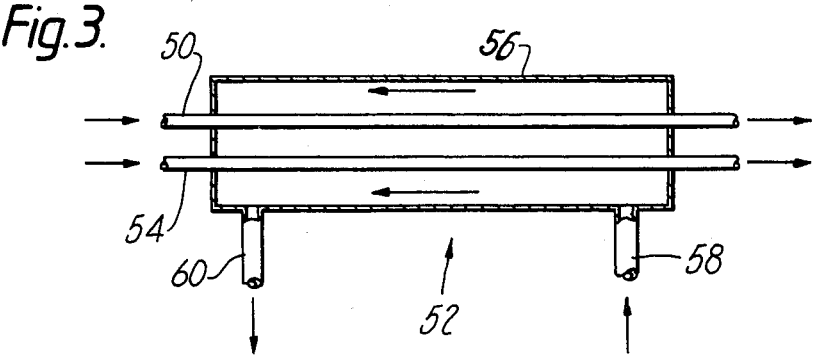
FIG. 3 is a schematic diagram of a means of apparatus according to the invention for reducing contaminant content of gases flowing therethrough.

The sample flow of gas is then directed to the inlet of first conduit means 50 of equilibrator means 52 and the reference flow of gas is directed to the inlet of second conduit means 54 of the equilibrator means, shown in detail in FIG. 3. Between these inlets, and outlets of the two conduit means, the two conduit means are enclosed within enclosure means provided by a cylindrical jacket 56 which also has an inlet 58 and an outlet 60.

At this stage, both the sample flow of gas and the reference flow of gas will both contain contaminant gases which, in the detector means, may mask detection of the constituent gas in the reference flow, and thus detection of its absence from the sample flow. These contaminants include, for example, water vapour, hydrogen, oxygen, organic substances in their vapour phases and light polar molecules.

The purpose of the equilibrator is to reduce the content of such contaminants in each of the sample flow and the reference flow and to ensure, insofar as is possible that the quantities of any contaminant which remains in the two flows of gas are equal. The conduit means are both formed of the same material and this material is permeable to the contaminant which it is desired to remove. Thus, for example, for the removal of water vapour and light polar molecules, the conduit means can be formed from a material such as that commercially available from E. I. Du Pont de Nemours & Co. Inc. under the trade mark "Naflon" which is believed to be a polymer of tetrafluoroethylene with a sulphuric acid group substituted for one of the fluorine radicals. For the removal of oxygen and the vapours of most organic substances which are likely to be encountered, the conduit means can be formed from a suitable silicone rubber, for example dimethyl silicone. If hydrogen is to be removed, then the conduit means are made of palladium which as is known in the art, is permeable to hydrogen when heated. It will, of course, be appreciated that if it is required the equilibrator means may include a succession of conduit means arranged in series so that provision is made for removal of all of these contaminants.

To accelerate removal of contaminants a scavenging gas is pumped through the jacket 56, to wash out contaminant which passes through the walls of the conduit means. Any gas which is inert, for example argon, may be used to remove the contaminant. The flow of inert gas, which, to increase the efficiency of the equilibrator means 52, is in the opposite direction to the direction of flow of the sample gas and reference gas, can be adjusted so as to allow the contaminants to be equally distributed throughout the jacket and thus in the two conduit means. This ensures that in subsequent measurements performed in the detector means, response to detection of any remaining contaminant in each flow will be substantially constant and minimal.

The sample gas issuing from the first conduit means will thus no longer contain the constituent to be detected nor a large proportion of contaminant while the reference gas will still contain the constituent, and the same proportion of any remaining contaminant as the sample gas.

From the outlets of the first and second conduit means, the two flows of gas, i.e. the sample gas flow and the reference gas flow, are conducted to either the valve control means 26 or to the detector means 24.

The arrangement of the detector means and the valve control means can take any one of the forms shown in FIGS. 4 to 8.

Figure 4:
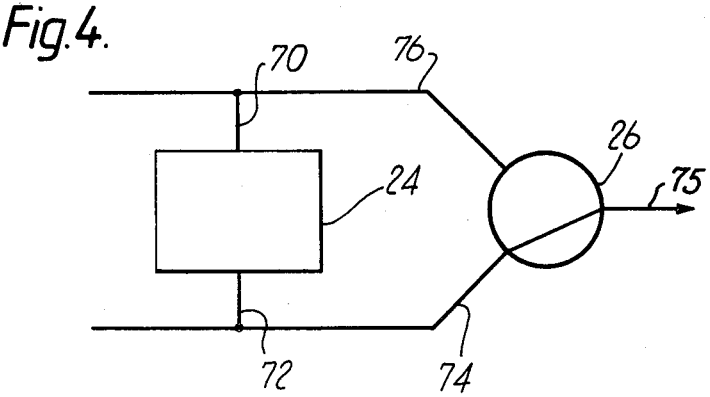

In the arrangement of FIG. 4, the detector means has a first inlet connector 70 and a second inlet connector 72, and the valve control means has a first inlet 76, a second inlet 74 and an outlet 75; and the first inlets of the detector means and of the valve control means are connected to the outlet of the first conduit means of the equilibrator means, while the second inlets of the detector means and of the valve control means are connected to the outlet of the second conduit means of the equilibrator means.

In the operation of the apparatus in carrying out a method according to the invention, and with the valve control means in the condition shown, i.e. its first condition, the reference gas will flow along conduit 74 and through the valve control means 26 to exhaust 75 while the sample flow will flow through conduit 76, and because the valve control means 26 closes off this conduit 76, through the detector means 24 into the conduit 74 for admixture with the reference gas. When the valve control means is moved to its second condition, the reference gas flows through the detector means while the sample gas flows through the conduit 76 to exhaust through the valve control means 26.

Figure 5:
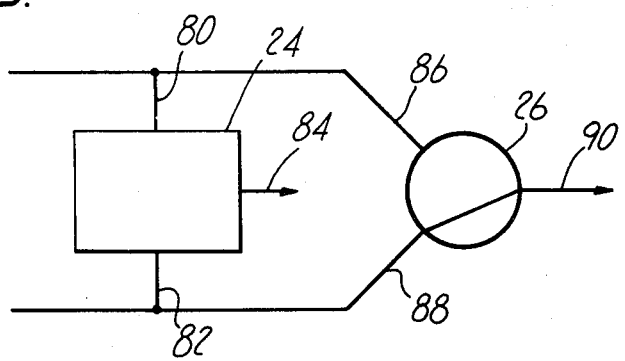

In the arrangement of FIG. 5, the detector means is shown as having a first inlet 80, a second inlet 82 and an outlet 84 while the valve control means has a first inlet 86, a second inlet 88 and an outlet 90.

The two first inlets 80, 86 are connected to the outlet of the first conduit means of the equilibrator means, and the two second inlets are connected to the outlet of the second conduit means thereof. As opposed to the arrangement of FIG. 4, with the valve control means of FIG. 5 shown in its first condition, sample gas flows into the first inlet 80 of the detector means 24 and exhausts from the outlet 84 while the reference gas exhausts directly through the valve control means 26 via its second inlet 88. When the valve control means is switched to its second condition, the sample gas exhausts directly through the valve control means via its first inlet 86 while the reference gas flows through the detector means.

In the arrangement of FIG. 6, the detector means has a single inlet 100 and an outlet 102, and the first conduit means of the equilibrator means is connected to this inlet 100 by first gas flow restrictor means 104 while the second conduit means is connected to the inlet 100 by second gas flow restrictor means 106. Both gas flow restrictor means 104, 106 are provided by narrower bore (and helically shaped) piping than the piping of the first and second conduit means. The valve means has a first inlet 108 connected to the first conduit means of the equilibrator means, a second inlet 110 connected to the second conduit thereof, and an outlet 112. As will be readily understood, without further detailed explanation, the manner of operation with this arrangement is substantially similar to that of FIG. 5.

In each of the arrangements of FIGS. 4, 5 and 6 the valve control means 26 can be provided by an electromagnetically controlled valve such as a Clippard Model EV03 12 V DC valve manufactured by Clippard Instrument Laboratory Inc. of Cinncinnati, Ohio, U.S.A., provided that it is used either downstream from or in parallel with the detector means. This type of valve has a rapid response time but has a comparatively large "dead" volume and has been found, in carrying out experiments, to contaminate gas flow due to some parts of the valve interior being made from materials which can be taken up by gas flow therethrough.

Figure 10:
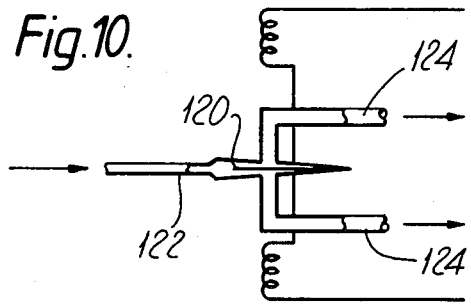
FIG. 10 is a schematic diagram of a form of valve means suitable for use in an apparatus according to the invention.
Figure 11:
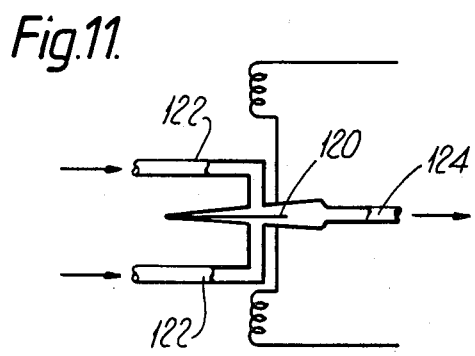
FIG. 11 is a schematic diagram of a second form of valve means suitable for use in an apparatus according to the invention.

If it is required to employ valve control means upstream of the detector means, then a valve such as that shown in FIG. 10 or FIG. 11 should be used. This type of valve would typically be made from inert material and have a magnetically operable flap 120 between its inlet(s) 122 and its outlet(s) 124. As will be readily understood from these two Figures, FIG. 10 illustrates such a valve having first and second inlets and an outlet while FIG. 11 illustrates a valve having a single inlet and first and second outlets.

The valve of FIG. 10 can be used with the arrangement of FIG. 7 wherein the first inlet 122 of the valve is connected to the first conduit means of the equilibrator means and the second inlet 122 is connected to the second conduit means thereof. By switching of the valve, the sample gas can flow through the valve into the detector means when the valve is in its first condition as illustrated while the reference flow is stopped, and when the valve is switched to its second condition, the reference flow will flow through the valve into the detector means while the sample flow is stopped.

The valve 128 of FIG. 11 can be used with the arrangement of FIG. 8 wherein its first outlet 124 is connected to the inlet of a first detector means 129 and its second outlet 124 is connected to the inlet of a second similar detector means 130. The inlet of the valve is connected to the first conduit means of the equilibrator means. A second identical valve 132 has its inlet connected to the second conduit means of the equilibrator means, its first outlet 124 connected to the inlet of the first detector means 129, and its second outlet 124 connected to the inlet of the second detector means 130. The advantage of this arrangement is that, while the valve 128 is in its first condition, as shown, and sample gas passes to the first detector means 129, reference gas flows to the second detector means through the second valve 132 which is in its second condition as shown, and, when the conditions of the two valves 128, 132 are switched simultaneously, the sample gas flows through the second detector means 130 while the reference gas flows through the first detector means 129, so that continuous measurement can be effected on each of the two gas flows.

Figure 9:
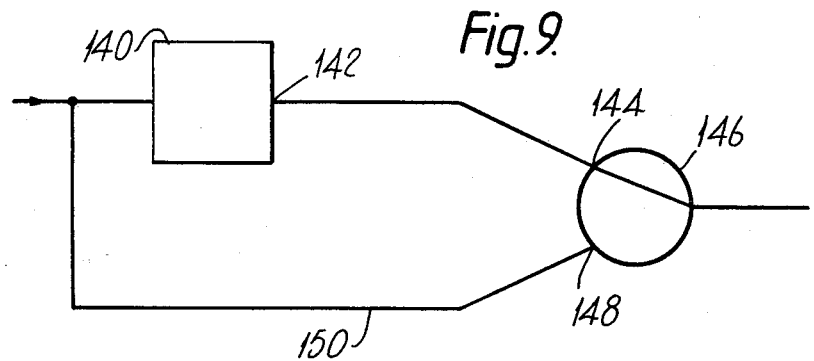
FIG. 9 is a schematic diagram illustrating another arrangement of valve control means and gas detector means for use in apparatus according to the invention.

In the arrangement of FIG. 9, a single inlet is provided to the detector means 140 whose outlet 142 is connected to a first inlet 144 of valve control means 146 having a second inlet 148 connected to a bypass line 150. With this arrangement the sample gas and the reference gas can be fed sequentially to the detector means 140 through the bypass line 150 so that the detector means can remain filled with either the sample gas or the reference gas when the valve is in its first condition, as shown, or either gas can flow through the bypass line 150, so that a detectable difference is observed.

The detector means of an apparatus according to the invention may be a thermal conductivity detector, a hot wire detector, a flame ionization detector, an electron capture detector, a gas density detector, an ion emission detector, or any detector which can be used where a sample gas has a component which can be destroyed or reduced and the sample gas then compared with a reference gas to detect the component of interest. Furthermore, as will be readily understood by those skilled in the art, apparatus and method according to the invention could be adapted or selected for the monitoring of liquids as well as gases.

An arrangement for controlling the operation of the reactor means, the detector means and the valve control means is shown in, for example, FIG. 2 of the drawings of U.K. Pat. No. 1,482,611, and will, therefore, not be further described.

I claim:

1. Apparatus for use in detecting a constituent fluid in very low concentrations in a sample flow of fluid, also containing at least one contaminant, the apparatus comprising first and second conduit means each having an inlet and an outlet and being formed of a material which is permeable to the at least one contaminant; enclosure means for enclosing the first and second conduit means substantially along the length thereof, the enclosure means having an inlet and an outlet whereby a diluent fluid can be passed through the enclosure means to remove contaminant diffused from the first and second conduit means into the enclosure means and whereby residual contaminant can be distributed equally between the first and second conduit means; detector means having a first inlet and an outlet; and valve control means for alternately allowing the sample flow of fluid from the first conduit means to pass through the detector means, when the valve control means is in a first condition, and a reference flow of fluid from the second conduit means to pass through the detector means, when the valve control means is in a second condition.

2. Apparatus according to claim 1 wherein the detector means has a second inlet, and the valve control means has a first inlet, a second inlet and an outlet, the first conduit means being connected to the first inlet of the detector means and to the first inlet of the valve control means, and the second conduit means being connected to the second inlet of the detector means and to the second inlet of the valve control means, whereby, when the valve control means is in its first condition, the reference flow of fluid passes through the valve control means to its outlet, and, when the valve control means is in its second condition, the sample flow of fluid passes through the valve control means to its outlet.

3. Apparatus according to claim 1 wherein the outlet of the detector means provides a second inlet, and the valve control means has a first inlet, a second inlet and an outlet, the first conduit means being connected to the first inlet of the detector means and to the first inlet of the valve control means and the second conduit means being connected to the second inlet of the detector means and to the second inlet of the valve control means, whereby when the valve control means is in its first condition, the sample flow of fluid passes from the first inlet to the second inlet of the detector means and, in admixture with the reference flow of fluid, passes through the valve control means to its outlet, and, when the valve control means is in its second condition, the reference flow of fluid passes from the second inlet to the first inlet of the detector means and, in admixture with the sample flow of fluid, passes through the valve control means to its outlet.

4. Apparatus according to claim 1 wherein the valve control means has a first inlet, a second inlet and an outlet, the apparatus further comprising a first fluid restrictor having an outlet connected to the inlet of the detector means, and an inlet, and a second fluid flow restrictor having an outlet connected to the inlet of the detector means, and an inlet, the first conduit means being connected to the inlet of the first fluid flow restrictor and to the first inlet of the valve control means, and the second conduit means being connected to the inlet of the second fluid flow restrictor and to the second inlet of the valve control means.

5. Apparatus according to claim 1 and further comprising second detector means having an inlet and an outlet, the valve control means having an inlet, a first outlet and a second outlet, the first outlet being connected to the inlet of the first detector means and the second outlet being connected to the inlet of the second detector means.

6. Apparatus according to claim 5 and further comprising second valve control means having an inlet and a first outlet and a second outlet, the first outlet of the second valve control means being connected to the first-mentioned detector means, and the second outlet of the second valve control means being connected to the second detector means, the two detector means each having an output and these outputs being connected in common, the inlet of the first valve control means being connected to the outlet of the first conduit means, and the inlet of the second valve control means being connected to the outlet of the second conduit means.

7. Apparatus according to claim 5 wherein the valve control means comprises an electromagnetically controlled movable-reed valve.

8. Apparatus according to claim 1 wherein the valve control means has a first inlet connected to the outlet of the first conduit means, a second inlet connected to the outlet of the second conduit means and an outlet connected to the inlet of the detector means.

9. Apparatus according to claim 1 wherein the valve control means has a first inlet, a second inlet and an outlet, the first conduit means being connected to the first inlet of the valve control means and to the inlet of the detector means, and the second conduit means being connected to the second inlet of the valve control means and to the inlet of the gas detector means.

10. Apparatus according to any one of claims 1 to 9 and further comprising fluid reactor means capable of effecting a chemical change in the constituent fluid in the sample flow of fluid, and having an inlet and an outlet, connected to the first conduit means, whereby the sample flow of fluid is introduced into the fluid reactor means upstream of the first conduit means, dummy fluid reactor means being similarly connected to the inlet of the second conduit means.

11. Apparatus according to claim 10 wherein fluid flow restrictor means is connected to the inlet of each of the fluid reactor means and the dummy fluid reactor means.

12. Apparatus according to claim 1 wherein the detector means is gas detector means for detecting the presence or absence of a constituent gas in a sample flow of gas also containing at least one gaseous contaminant.

13. Apparatus according to claim 1 or 12 wherein the material of the first and second conduit means is permeable to water and light polar molecules only.

14. Apparatus according to claim 1 or 12 wherein the material of the first and second conduit means comprises a silicone rubber permeable to oxygen and vapours of selected organic substances.

15. Apparatus according to claim 1 or 12 wherein the material of the first and second conduit means comprises palladium.

16. Apparatus according to claim 1 wherein the detector means has means for providing an electrical signal representative of fluid flow through detector means; and means is provided for interpreting signals received from the detector means when the sample flow of fluid and the reference flow of fluid pass through the detector means to provide an output to indicate when the constituent fluid to be identified is in the sample flow, and when it is absent.

17. A method of detecting a constituent fluid in a sample flow of fluid also containing at least one contaminant, the method comprising the steps of:
(a) directing the sample flow of fluid along first conduit means;
(b) directing a reference flow of fluid along second conduit means; the first and second conduit means each being formed of a material which is permeable to the at least one contaminant and being enclosed substantially along the length thereof by enclosure means having an inlet and an outlet;
(c) passing a fluid through the enclosure means to wash out therefrom contaminant which has diffused through the first and second conduit means;
(d) alternately directing the sample flow of fluid and the reference flow of fluid to fluid detector means; and
(e) monitoring electrical signals from the fluid detector means to determine when the constituent fluid is present in the fluid detector means and when it is absent.

18. A method according to claim 17 wherein step (d) is carried out by operating valve control means synchronized with the fluid detector means.

19. A method according to claim 18 wherein the detector means has a first inlet, a second inlet, and an outlet and the valve control means has a first inlet, a second inlet and an outlet, the first inlets of the detector means and the valve control means communicating with the first conduit means and the second inlets of the detector means and the valve control means communicating with the second conduit means, whereby step (d) is carried out by directing the sample flow of fluid through the first conduit means and the first inlet and the outlet of the detector means while the reference flow of fluid is directed through the second conduit means and the second inlet and the outlet of the valve means, and then by directing the sample flow of fluid through the first conduit means and the first inlet and the outlet of the valve control means, while the reference flow of fluid is directed through the second conduit means and the second inlet and the outlet of the detector means.

20. A method according to claim 18 wherein the detector means has a first connector, and a second connector, and the valve control means has a first inlet, a second inlet and outlet, the first connector, and the first inlet of the valve control means communicating with the first conduit means, and the second connector, and the second inlet of the valve control means communicating with the second conduit means, whereby the sample flow of fluid is directed through the first conduit means and the first and second connectors into the second conduit means while the reference flow of fluid is directed through the second conduit means and the second inlet and the outlet of the valve control means, and the sample flow of fluid is directed through the first conduit means and the first inlet and the outlet of the valve control means, while the reference flow of fluid is directed through the second conduit means and the first and second connectors into the first conduit means.

21. A method according to claim 18 wherein two valve control means and a second detector means are provided, each valve control means having an inlet and first and second outlets, and each detector means having an inlet and an outlet, the first outlet of both valve control means being connected to the inlet of the first detector means, and the second outlet of both valve control means being connected to the inlet of the second detector means, whereby step (d) is carried out by directing the sample flow of fluid through the first outlet of the first valve control means and through the first detector means while the reference flow through the second outlet of the second valve control means and through the second detector means, and by directing the sample flow of fluid through the second outlet of the first valve control means and through the second detector means, while the reference flow is directed through the first outlet of the second valve control means and through the first detector means.

22. A method according to any one of claims 17 to 21 wherein prior to step (a) the sample flow of fluid is passed through fluid reactor means capable of effecting a chemical change in the constituent fluid in the sample flow.

23. A method according to claim 22 wherein prior to step (b) the reference flow of fluid is passed through dummy fluid reactor means.

24. A method according to claim 17 wherein the fluid is gaseous.

25. A method according to claim 24 wherein the material of the first and second conduit means is permeable to water and light polar molecules only.

26. A method according to claim 24 wherein the material of the first and second conduit means comprises a silicone rubber permeable to oxygen and vapours of selected organic substances present in the sample flow of gas and the reference flow of gas as contaminant.

27. A method according to claim 24 wherein the material of the first and second conduit means comprises palladium permeable to hydrogen present in the sample flow of gas and the reference flow of gas as contaminant.

28. A method according to any one of claims 24 to 27 wherein the rate of flow of washing fluid through the enclosure means, in carrying out step (c), is such as to allow the quantities of any contaminant present in the first and second conduit means to become substantially equal.

* * * * *